(12) United States Patent
Doan et al.

(10) Patent No.: US 7,899,550 B1
(45) Date of Patent: Mar. 1, 2011

(54) APPARATUS AND METHOD FOR TRANSSEPTAL FIXATION

(75) Inventors: Phong D. Doan, Stevenson Ranch, CA (US); Xiangqun Chen, Valencia, CA (US); Apratim Dixit, Woodland Hills, CA (US); Virote Indravudh, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1053 days.

(21) Appl. No.: 11/466,087

(22) Filed: Aug. 21, 2006

(51) Int. Cl.
*A61N 1/06* (2006.01)

(52) U.S. Cl. ........................................... 607/122

(58) Field of Classification Search ............... 607/17, 607/119, 122; 600/488, 485, 506
See application file for complete search history.

(56) References Cited

U.S. PATENT DOCUMENTS

| 5,353,800 | A | 10/1994 | Pohndorf et al. | |
|---|---|---|---|---|
| 7,274,965 | B1 * | 9/2007 | Karicherla et al. | 607/119 |
| 2004/0147969 | A1 | 7/2004 | Mann et al. | |
| 2004/0167580 | A1 | 8/2004 | Mann et al. | |
| 2005/0136385 | A1 | 6/2005 | Mann et al. | |
| 2005/0165344 | A1 | 7/2005 | Dobak, III | |
| 2005/0165456 | A1 | 7/2005 | Mann et al. | |
| 2005/0288596 | A1 * | 12/2005 | Eigler et al. | 600/485 |
| 2005/0288604 | A1 | 12/2005 | Eigler et al. | |
| 2005/0288722 | A1 | 12/2005 | Eigler et al. | |
| 2006/0009810 | A1 | 1/2006 | Mann et al. | |
| 2006/0224224 | A1 * | 10/2006 | Muhlenberg et al. | 607/122 |

FOREIGN PATENT DOCUMENTS

| WO | 2005000206 | A2 | 1/2005 |
|---|---|---|---|
| WO | 2005000206 | A3 | 1/2005 |
| WO | 2005107583 | A2 | 11/2005 |
| WO | 2006029370 | A2 | 3/2006 |

* cited by examiner

*Primary Examiner*—Niketa I Patel
*Assistant Examiner*—Rex Holmes

(57) ABSTRACT

A lead implanted across a heart wall such as an atrial septum includes structure for fixation to the wall. In some embodiments the distal end of the lead includes a sensor for measuring quantities such as pressure at a distal side of the wall. The fixation structures may be positioned on opposite sides of the wall after implant. The fixation structures may be aligned with the lead during delivery of the lead to the implant site and expanded from the lead at the implant site.

4 Claims, 14 Drawing Sheets

APPARATUS AND METHOD FOR TRANSSEPTAL FIXATION

TECHNICAL FIELD

This application relates generally to implantable cardiac stimulation devices and, in some embodiments, to an apparatus and method for transseptal fixation.

BACKGROUND

When a person's heart does not function normally due to, for example, a genetic or acquired condition, various treatments may be prescribed to correct or compensate for the condition. For example, pharmaceutical therapy may be prescribed for a patient or a pacemaker may be implanted in the patient to improve the function of the patient's heart.

In conjunction with such therapy it may be desirable to measure pressure in one or more chambers of the heart. For example, cardiac pressure may be used as an indicator for several cardiac conditions. By measuring cardiac pressure, conditions such as these may be detected and in some cases the patient's therapy may be modified to compensate for the abnormal conditions. As an example, if cardiac pressure is measured over time, the operation of an implanted cardiac device such as a pacemaker or cardioverter/defibrillator (ICD) may be adjusted, as necessary, according to conditions diagnosed as a result of the pressure measurements.

While pressure sensing devices for measuring pressures on the right side of the heart are well known, for some conditions it may be more desirable to obtain pressure readings from the left side of the heart. For example, left atrial pressure has been identified as a potential indicator for left ventricular failure.

It has been proposed to measure left side atrial pressure by implanting a sensor across the atrial septum from the right atrium. However, implantation techniques such as this may present certain dangers to a patient. For example, during the implant procedure or after the sensor has been implanted there is a potential risk of stroke caused by thrombosis formation and/or damage to the septum. Moreover, long term stability of any anchoring mechanism used for the sensor is important for proper functioning of the implanted sensor and, ultimately, for the patient's safety. For example, if the sensor is not securely fixed in place, the reliability of the sensor may be compromised. This, in turn, may negatively impact the accuracy of any pressure readings used for subsequent treatment of the patient. Accordingly, there is a need in transseptal applications for safe delivery devices, safe delivery procedures and reliable fixation mechanisms.

SUMMARY

A summary of selected aspects and/or embodiments of an apparatus constructed or a method practiced according to the invention follows. For convenience, an embodiment of an apparatus constructed or a method practiced according to the invention may be referred to herein simply as an "embodiment."

The invention relates in some aspects to a structure for fixing an apparatus to a wall of a heart. For example, a structure may be employed to anchor an apparatus that is implanted through a septal wall (e.g., atrial septum or ventricular septum). A structure also may be employed to anchor an apparatus to a septal wall. For convenience, such a structure may be referred to herein simply as an anchor.

In some embodiments an anchor is incorporated into a lead including a sensor at its distal end. The lead is routed to the septal wall such that the sensor is implanted through or adjacent to the septal wall. The anchor serves to fix the lead (e.g., the sensor) to the septal wall.

In some embodiments anchors are adapted to be positioned against opposite sides of a septal wall. The anchors may be expandable such that they lie relatively flat against or in a lead during delivery and expand away from the lead upon implant. For example, the anchors may be predisposed to extend (e.g., at substantially a right angle) from the lead.

In some embodiments an anchor is relatively flat to facilitate being bent against the lead so that the lead may be inserted into a sheath for delivery to the implant site. For example, an anchor at a distal position on the lead is adapted to bend forward (e.g., in a distal direction) and an anchor at a relatively proximal position on the lead is adapted to bend backward (e.g., in a proximal direction) when the lead is inserted into a sheath for delivery.

In some embodiments the anchor comprises a long, slender member having elastic properties such that the anchor may lie relatively flat against or in a lead during delivery and expand away from the lead upon implant. Here, the anchor may be slideable relative to the lead such that as the anchor is extended from a distal portion of the lead, the anchor expands (e.g., to a predisposed orientation) away from the lead. In some embodiments the anchor expands to a spiral orientation that is at (or substantially at) a right angle with respect to the axis of the lead. In some embodiments this anchor compromises a distal anchor. In some embodiments the expanded anchor clamps a portion of the septal tissue around a distal end of the lead.

In some embodiments a lead includes a proximal anchor that is slideable relative to the lead. Upon implant the proximal anchor is slid in a distal direction to engage the proximal side (e.g., the right atrial side) of the septum. The lead and/or anchor may incorporate one or more locking mechanisms (e.g., locking structure) to hold the slideable anchor in place relative to the lead when the slideable anchor is at certain positions along the lead. In some embodiments a locking mechanism comprises one or more ribs on one component (e.g., at a given location on the lead body) that mate with corresponding grooves on another component (e.g., the slideable anchor). In some embodiments a locking mechanism comprises one or more directional barbs on one component (e.g., the slideable anchor) that interact with another component (e.g., the lead body) so that the slideable anchor only slides in the distal direction along the lead.

BRIEF DESCRIPTION OF THE DRAWINGS

These and other features, aspects and advantages of the invention will be more fully understood when considered with respect to the following detailed description, appended claims and accompanying drawings, wherein:

FIG. 14, including

Figure 1:
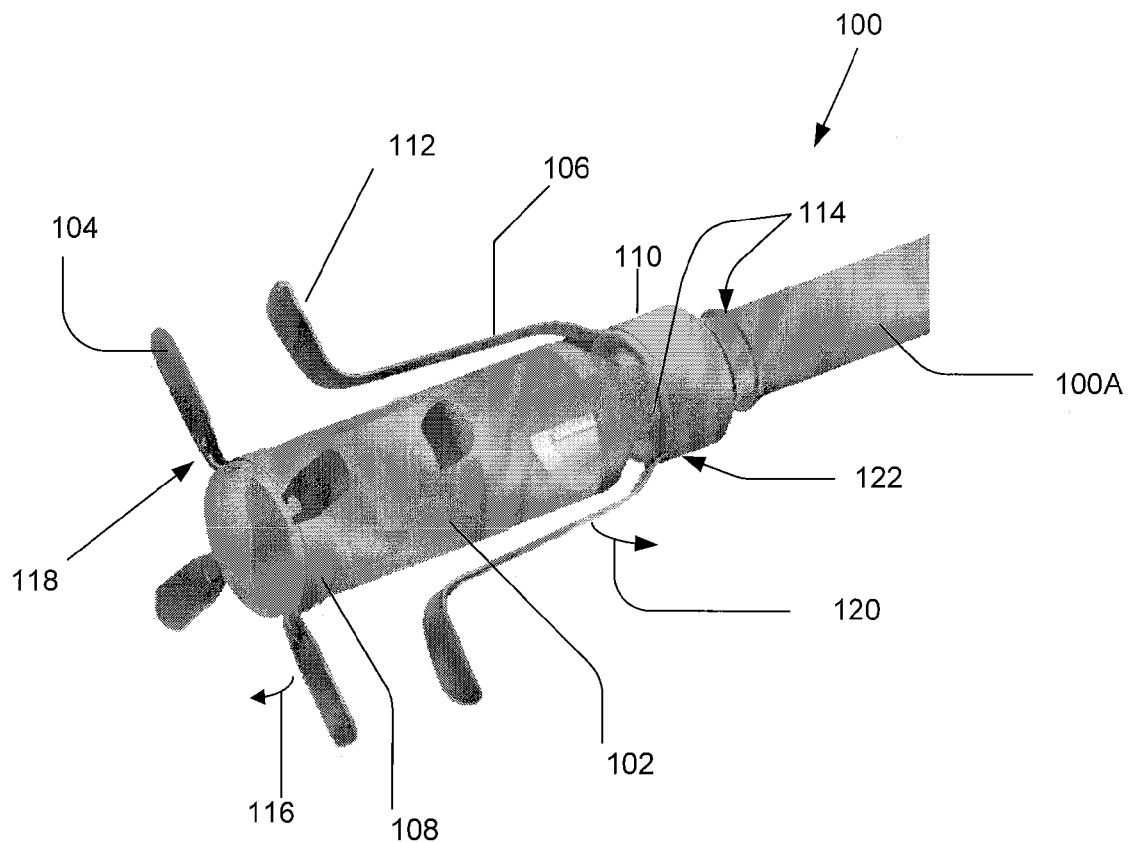
FIG. 1 is a simplified diagram of one embodiment of a lead including distal and proximal anchors.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

Aspects of the invention are described below, with reference to detailed illustrative embodiments. It will be apparent that the invention may be embodied in a wide variety of forms, some of which may be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s). Accordingly, references to "an" or "one" embodiment in this discussion are not necessarily to the same embodiment, and such references mean at least one embodiment.

Referring to FIG. 1, in some aspects the invention relates to a cardiac lead 100 that may be implanted in a patient. A proximal end of the lead 100 may connect to an implantable cardiac device (not shown) such as an implantable cardioverter defibrillator ("ICD"). The implantable cardiac device may provide therapy such as cardiac pacing or defibrillation for the patient.

The lead 100 provides cardiac pressure signals to circuitry in the implantable device that processes the signals to calculate the corresponding cardiac pressure. The implantable cardiac device uses the pressure information in conjunction with a prescribed therapy plan. For example, left atrial pressure readings may be used as an indicator of left ventricular failure. In this case, the implantable cardiac device may adjust its therapy (e.g., stimulation, drug delivery, etc.) or generate an alert (e.g., sent to a device external to the patient) when certain pressure values are measured.

In the embodiment of FIG. 1 the lead 100 consists of a lead body 100A and includes one or more sensors (referred to herein for convenience as sensor 102) for measuring pressure in the patient. In some embodiments the lead 100 also may include one or more electrodes (not shown) for sensing signals in the patient's heart and/or for providing stimulation signals (e.g., for pacing and/or shocking) to the heart.

The lead 100 is adapted to take pressure readings across a wall of the heart. For example, in embodiments where the lead 100 is initially routed into the right side of the heart, pressure may be measured in the left side of the heart (e.g., the left atrium, left ventricle or aorta) by routing the lead 100 through a hole made in the heart wall (e.g., the ventricular septum or the atrial septum). For example, a hole may be created in the septum by piercing the septum using a separate piercing device. A distal portion of the lead 100 is thus maneuvered through the hole in the septum. For convenience the term septum may be used hereafter to refer to any wall of the heart. It should be appreciated, however, that the teachings herein are not necessarily limited to applications involving the ventricular septum or the atrial septum.

The lead 100 includes one or more fixation structures (e.g., anchors 104 and 106) that extend from the lead body 100A and/or the sensor 102. The anchors 104 and 106 are adapted to be positioned against a distal wall and a proximal wall, respectively, of the septum. An anchor may take many forms including, without limitation, tine-like structures, thin elongated members (e.g., wire-like structure) or other suitable members that may protrude from the lead.

The anchors may be positioned a given distance apart on the lead 100 to enable the anchors to effective engage the septum. For example, the lead 100 may be constructed so that the spacing between the tines on the anchor 104 and the end portions 112 of the anchors 106 is approximately equal to (or slightly less than) the thickness of the septum at the implant site. In some patients this thickness is approximately 3-4 mm in the area of the fossa ovalis.

At least a portion of an anchor may be configured to provide a relatively low profile against the septal wall. For example, as shown in FIG. 1 the anchor 104 includes several relatively flat tines (i.e., having a relatively flat cross section) that are oriented perpendicular to the longitudinal axis of the lead 100. Hence, the anchor 104 may lie relatively flat against the distal side of the septum. Similarly, a portion 112 of each tine of the anchor 106 is adapted to lie relatively flat against the proximal side of the septum. By maintaining a low profile, problems that may otherwise be caused by components that protrude from the wall of the heart may be avoided. For example, blood clots may form on an object that protrudes from a wall of the heart. If these blood clots break loose in the left side of the heart the blood clots may travel to other areas of the body such as the brain and cause a blockage in a blood vessel (i.e., an embolism).

In contrast, the body may quickly build up a biological layer of endothelial cells ("the intima") over an anchor with a relatively low profile. As a result, the likelihood of blood clots breaking loose may be significantly reduced with a low profile lead as compared to leads that protrude relatively deeply into the left side of the heart. The buildup of the intima also may assist in firmly attaching the anchor to the septal wall. As a result, the lead may be attached to the heart in a sufficiently stable manner so as to prevent injury to the heart and provide accurate pressure measurements.

An anchor may be incorporated into a lead in a variety of ways. For example, an anchor may be attached to, inserted within or formed as part of a lead or any component of the lead. In the embodiment shown in FIG. 1 the anchor 104 is attached to the sensor 102 via a ring-like member 108. The member 108 may attach to the sensor in a variety of ways. For example, the member 108 may be welded or adhered to (e.g., using an adhesive) an outer surface of a housing for the sensor 102.

The anchor 106 is attached to the lead body 100A via a ring-like member 110. The member 110 also may attach to the lead body 100A in a variety of ways. For example, the member 110 may be welded or adhered to (e.g., using an adhesive) an outer surface of the lead body 100A. Alternatively, the member 110 and/or the lead body 100A may include a fixation structure 114 to fix the anchor 106 to the lead body 100A. For example, as shown in FIG. 1 the lead body 100A may include one or more ribs that tend to grip the member 110 or otherwise impede movement of the anchor 106 relative to the lead body 100A.

The invention also relates in some aspects to anchors that are adapted to reorient between multiple positions. For example the anchors 104 and 106 may be adapted to be disposed between the orientation shown in FIG. 1 (e.g., extending in a direction that is substantially perpendicular to the axis of the lead body 100A) and an orientation where the anchors 104 and 106 lie substantially parallel to the lead 100. For example, the anchors 104 and 106 may be configured to lie against the lead 100 as the lead 100 is delivered to the implant site. In this way, the distal end of the lead 100 has a smaller profile (e.g., cross section) during implant thereby facilitating routing the lead 100 through, for example, the venous system. Once, the distal end of the lead 100 is at the implant site (e.g., in a heart chamber or across heart chambers) the anchors 104 and 106 may be reconfigured to the orientation shown in FIG. 1.

In some embodiments the anchors 104 and 106 may be predisposed to the orientation shown in FIG. 1 where the anchors extend from the lead 100. In this case, as the distal end of the lead 100 is routed to the implant site the anchors 104 and 106 may be held by an appropriate mechanism to lie parallel to the lead body 100A. Once the implant site is reached, the anchors 104 and 106 may be allowed to return to their predisposed orientation.

Figure 2:
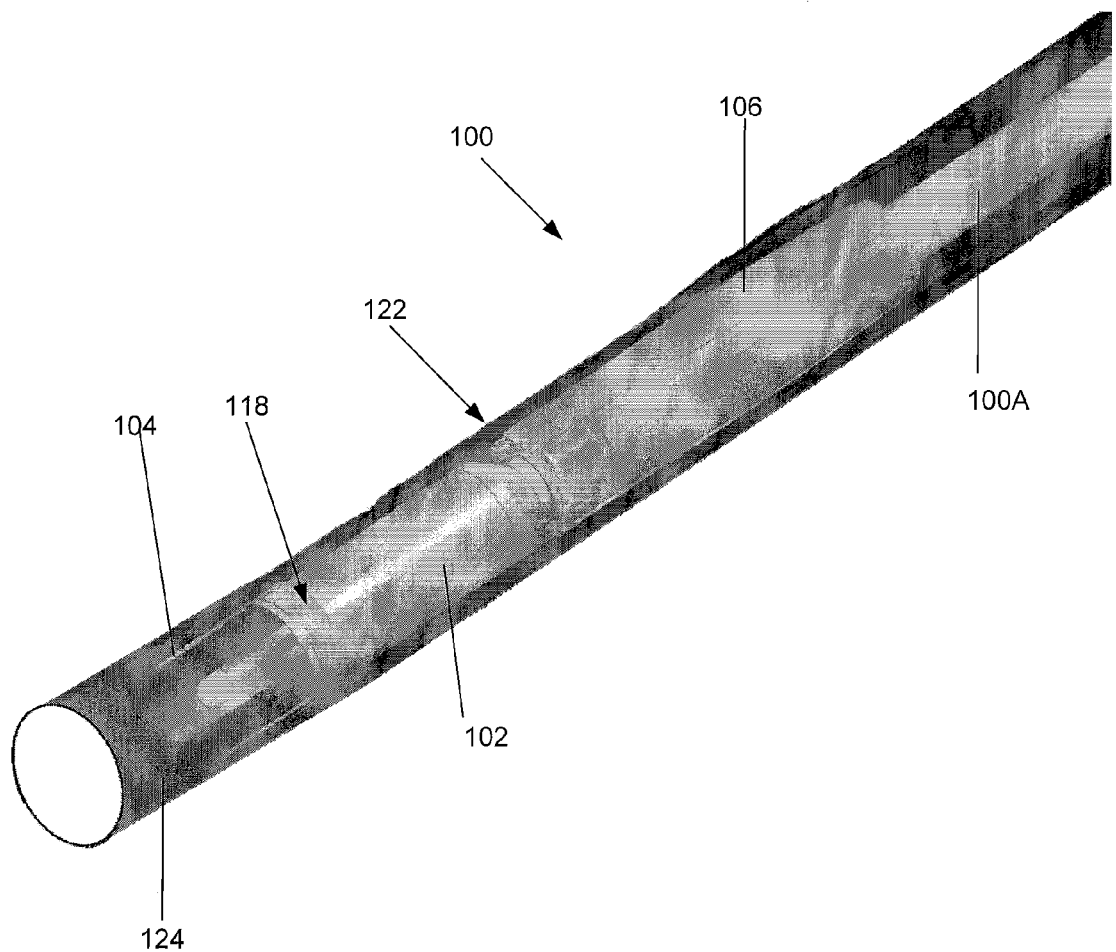
FIG. 2 is a simplified diagram of one embodiment a lead in a delivery sheath.

FIG. 2 illustrates an embodiment where the anchors 104 and 106 are folded to lie within a sheath 124 that is used to deliver the lead 100 to the implant site. Here, the tines of anchor 104 have been bent forward (in a distal direction) as represented by the arrow 116 in FIG. 1. To this end, a portion 118 of each tine of the anchor 104 is adapted to bend. For example, as shown more clearly in FIG. 2, each portion 118 may have a cutout to facilitate bending the tine in that area.

Conversely, the tines of anchor 106 have been bent backward (in a proximal direction) as represented by the arrow 120 in FIG. 1. To this end, a portion 122 of each tine of the anchor 106 is adapted to bend. Again, as shown more clearly in FIG. 2, each portion 122 may have a cutout to facilitate bending the tine in that area. In addition, each tine (or at least the bent portion of each tine adjacent the portion 112) may be sufficiently flexible to enable each tine to substantially flatten for placement in the sheath 124.

Once the distal end of the sheath 124 has been delivered to the implant site (i.e., through the septum), the anchor 104 may be released from the sheath 124 on the distal side of the septum. For example, the distal end of the lead 100 may be pushed in a distal direction (e.g., by holding the sheath 124 at a proximal end and pushing on the lead 100 or a stylet inserted into the lead at the proximal end) to release the anchor 104. Alternatively, the lead 100 may be held in place (e.g., by holding the lead 100 or a stylet inserted into the lead 100 at a distal end) while withdrawing the sheath 124.

Next, the sheath 124 may be withdrawn to release the anchor 106. Here, the lead 100 is positioned such that the anchor 106 will be deployed on the proximal side of the septum.

Orienting the anchor 106 in a proximal direction may advantageously simplify the implant procedure and enable the anchors 104 and 106 to more effectively hold the lead 100 onto the septum. For example, since the portions 112 of the anchor 106 that engage the septum are positioned proximally to the fulcrum point (i.e., portion 122) of the bent anchor 106, the anchor 106 may potentially be released as long as the portions 112 are positioned on the proximal side of the septum and the anchor 104 is positioned on the distal side of the wall. Hence, less precision may be needed regarding the position (in a longitudinal direction) of the lead 100 as compared to applications where a proximal anchor would bend in a distal direction. In the latter case, the lead 100 may need to be relatively precisely located so that the entire (or substantially the entire) proximal anchor is on the proximal side of the septum.

Moreover, by providing the anchor 106 with a sufficient amount of spring or tension action (or a similar force mechanism) at the bending portion 122, the proximal anchor 106 may be adapted to push against the proximal side of the septum once the proximal anchor 106 engages the septum. In this way, the action of the proximal anchor 106 may serve to firmly hold the septum between the distal anchor 104 and the proximal anchor 106 while automatically adjusting to the thickness of the septum.

Figure 3:
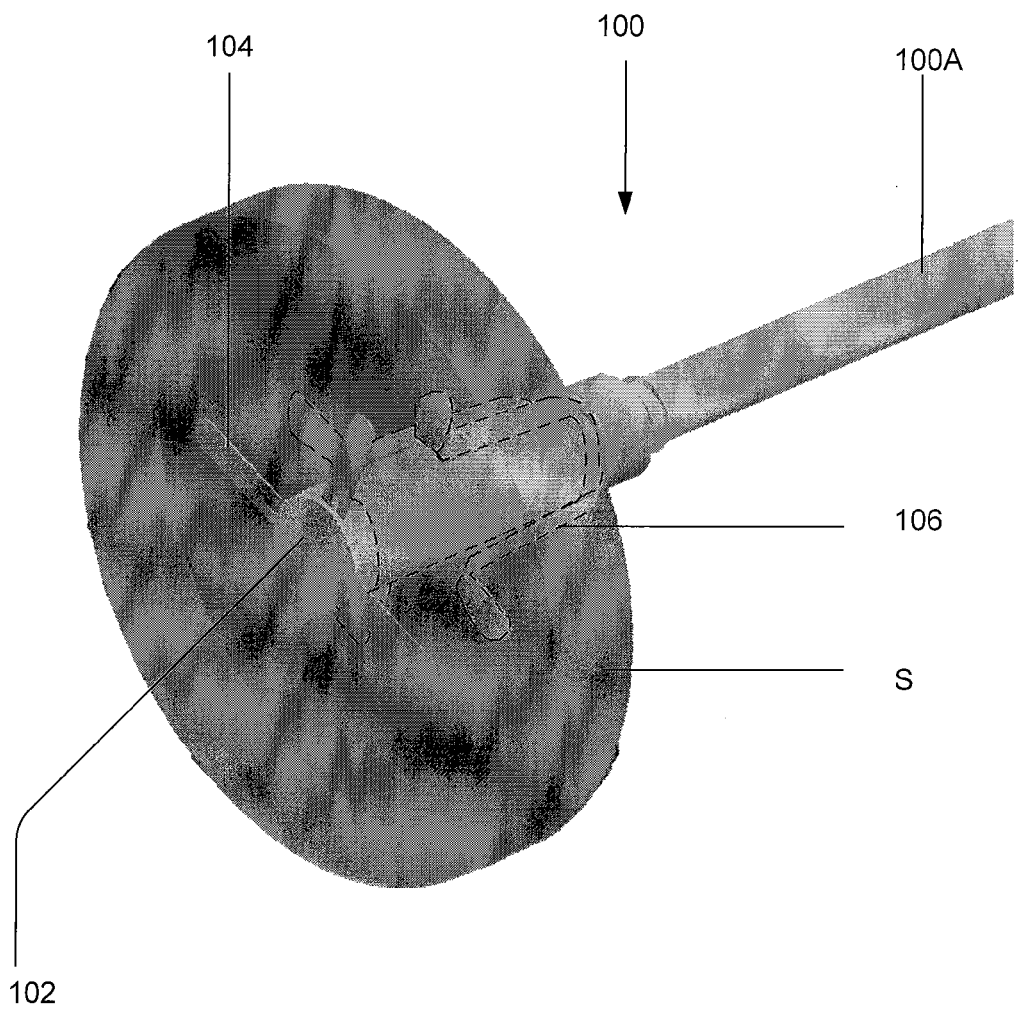
FIG. 3 is a simplified diagram of one embodiment of a lead including distal and proximal anchors implanted across a wall of a heart.

FIG. 3 illustrates an example of the lead 100 after is has been implanted across a septum S. In FIG. 3 the septum S is depicted in a simplified cut out manner. FIG. 3 illustrates that the anchor 104 engages the distal side of the septum S while the anchor 106 engages the proximal side of the septum S.

FIG. 3 also illustrates that the distal end of the lead 100 is exposed to the distal side of the septum. Accordingly, the sensor 102 may obtain pressure readings (e.g., via a diaphragm on the distal end of the sensor 102) from the distal side of the septum S (e.g., a heart chamber such as the left atrium or left ventricle). It should be appreciated that other mechanisms may be employed to couple the sensor 102 to the distal side. For example, the lead may incorporate one or more passages (e.g., filled with a fluid or a sufficient pressure wave transmitting material) to couple pressure waves from the distal end of the lead 100 to the sensor 102.

The sensor 102 may be integrated into the lead 100 in a variety of ways. For example, a sensor housing may be welded to or adhered to (e.g., using an adhesive) the lead body 100A. In some embodiments the sensor 102 may be located within the lead body 100A. In this case, the anchor 104 may attach to an outside surface of the lead body 100A or otherwise be coupled to the lead body 100A.

A typical pressure sensor generates electrical signals indicative of changes in a sensed pressure. Accordingly, one or more wires may run through a lumen (not shown in FIGS. 1-3) in the lead body 100A to connect the sensor 102 to an implantable cardiac device.

In addition, as discussed above, a lead may include one or more electrodes. An electrode may be located, for example, at a location on the lead such that the electrode interacts with the septum or at any other desirable location on the lead 100. In this case, the lead 100 also may include one or more wires routed through a lumen (not shown) in the lead body 100A to connect the electrode(s) to an implantable cardiac device.

The lead 100 and its associate components may be constructed of a variety of suitable materials. For example, the lead body may be made from conventional implantable lead materials including polymers such as silicone or polyurethane or some other suitable material. In some embodiments the anchors 104 and 106 are constructed at least in part of a flexible, biocompatible material. In some embodiments an anchor is made from a memory shape material such that the anchor readily reverts to a predisposed orientation. For example, an anchor may be made of a memory metal such as Nitinol.

It should be appreciated that the description above provides but a few examples of structures that may be used to fix a lead that is implanted through a septum. For example, mechanisms other than those specifically described here may be employed as anchors or to facilitate reorientation of the anchors in accordance with the teachings herein.

Figure 4:
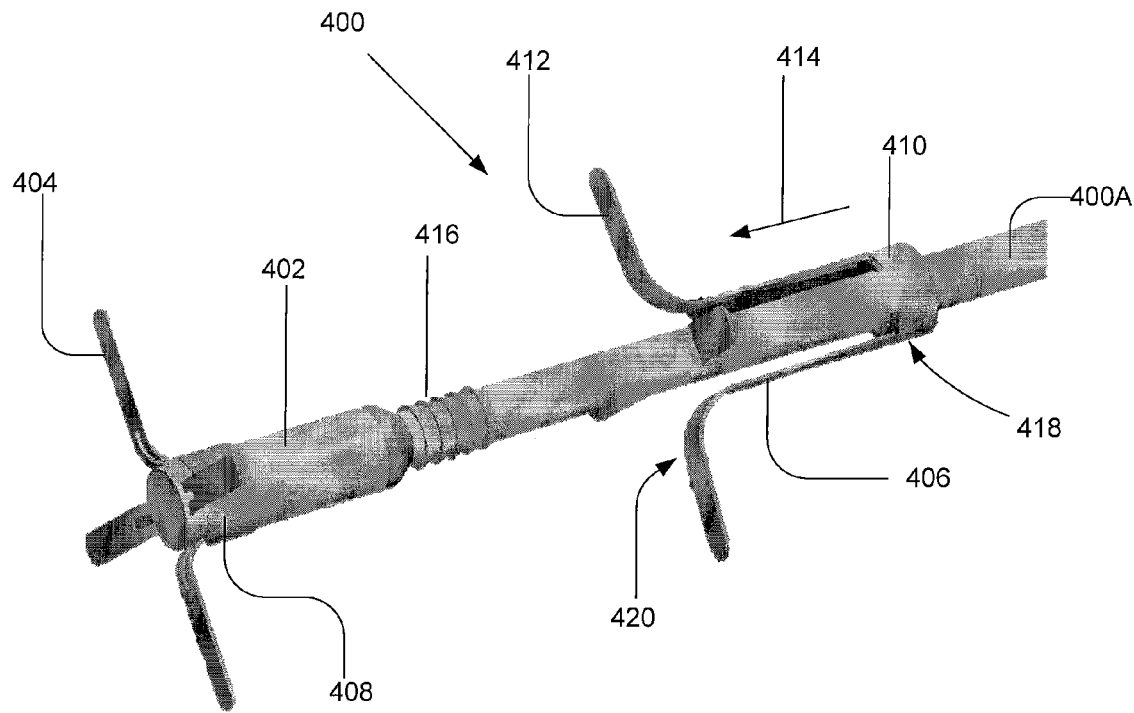
FIG. 4 is a simplified diagram of one embodiment of a lead including a slideable anchor.

FIG. 4 illustrates one embodiment of a lead 400 that includes an anchor that is moveable. The lead 400 may include components that are similar to the components of lead 100 and be constructed in a similar manner as discussed above. For example, the lead may include a lead body 400A, a pressure sensor 402 and a distal anchor 404 with a ring-like fixation member 408 as above.

In this embodiment, however, a proximal anchor 406 is adapted to slide relative to the lead body 100A. For example, a ring-like member 410 of a proximal anchor 406 may be slideably attached to the lead body 400A. In the example of FIG. 4, an inner surface of the member 410 slides over an outer surface of the lead body 400A. The proximal anchor 406 may thus be positioned against the septum to, for example, adjust the anchors 404 and 406 to the thickness of the septum.

The use of a slideable proximal anchor 106 may simplify the implant procedure. One such simplification may result, at least in part, from the proximal anchor 406 initially being positionable some distance away from the distal anchor 404. Here, it may be possible in some embodiments to position the deployed distal anchor 404 any reasonable distance beyond the septum without impacting where the proximal anchor 406 may be deployed. In contrast, in embodiments without a slideable proximal anchor, the distal anchor may need to be positioned very close to the septum when deploying the proximal anchor. Hence, the embodiment of FIG. 4 may enable the implant procedure to be performed more quickly and/or with less accurate and hence, less expensive, imaging equipment.

Moreover, the use of a slideable anchor 406 may provide one or more advantages related to the construction and/or operation of the anchors. For example, the lead 400 may be routed to the implant site as discussed above with the distal anchor 404 and the proximal anchor 406 folded to lie relatively parallel to the lead 400. As discussed above in conjunction with FIG. 2, the anchor 404 may be folded in a distal direction and the anchor 406 may be folded (e.g., at portion 418) in a proximal direction. Moreover, in the embodiment of FIG. 4 the anchors 404 and 406 may be folded in a proximal direction and a distal direction, respectively, without negatively impacting the implant procedure.

As discussed above, given the potential initial distance between the anchors, the distal anchor 404 may be inserted a reasonable distance beyond the septum. Consequently, the distal anchor 404 may be inserted far enough past the septum to enable deployment of distal anchors that are folded back (proximal direction) in the sheath (e.g., sheath 124). Thus, in the event such an orientation provides an advantage (e.g., in the construction of the anchor), such a configuration may be readily provided without impacting deployment of the proximal anchor 406.

In addition, the proximal anchor 406 may advantageously be adapted to fold in a distal direction. For example, the proximal anchor 406 may be bent at portion 420 such that the proximal anchor 406 lies substantially parallel to (e.g., lies against) the lead body 400A. This is practical in the embodiment of FIG. 4 given that the proximal anchor 406 may be initially positioned some distance away from the distal anchor 404 in the proximal direction and, as a result, the entire proximal anchor 406 may be deployed proximally from the septum. Consequently, less strain may be imparted on the proximal anchor 406 in this embodiment because the proximal anchor 406 may only be bent slightly at portion 420 as opposed to being bent significantly at portion 418 as discussed above.

Figure 5:
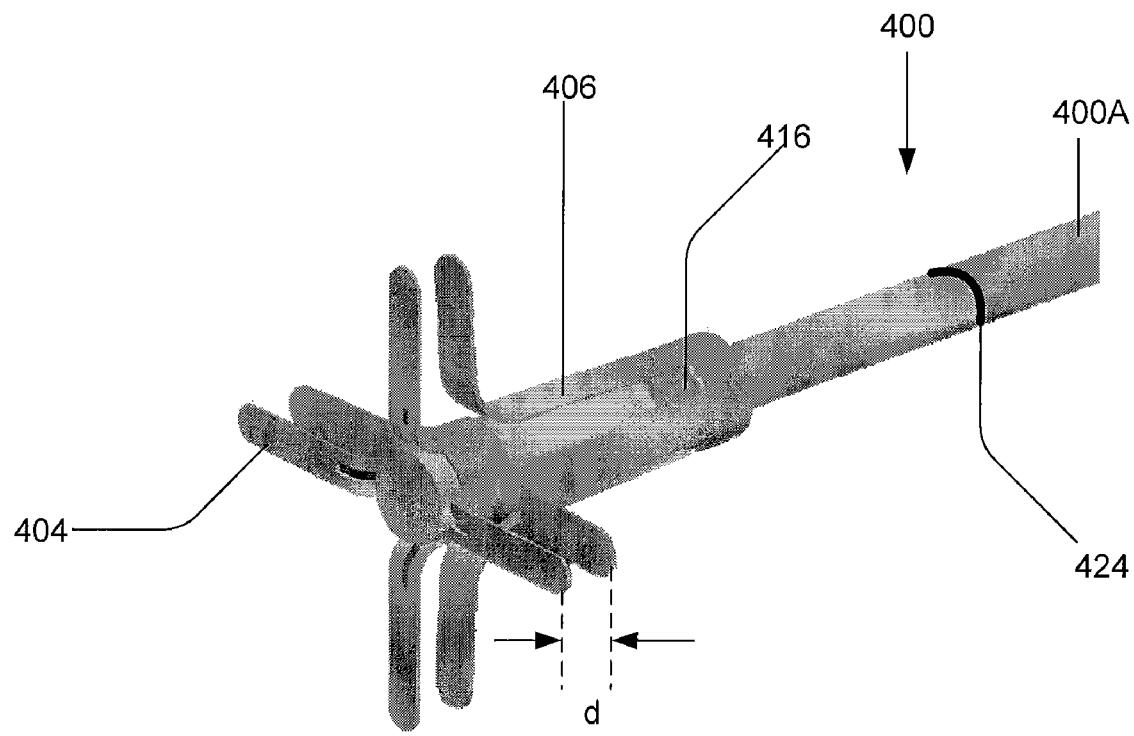
FIG. 5 is a simplified diagram of one embodiment of a lead including a slideable anchor and a locking mechanism.

As illustrated in FIG. 4, once the sheath is withdrawn in the proximal direction the distal anchor 406 will be deployed. As shown in FIG. 5, the lead 400 may include a structure 424 to prevent the proximal anchor 406 from traveling too far in the proximal direction when the sheath is being withdrawn.

Once both anchors are deployed, the proximal anchor 406 may be slid in the direction indicated by arrow 414 so that the relatively perpendicular portion 412 of the proximal anchor 406 engages the septum. Various mechanisms may be employed to move the proximal anchor 406. For example, in some embodiments, once the proximal anchor 406 has been deployed from the sheath (e.g., sheath 124), the sheath may be pushed in a distal direction to push the proximal anchor 406 towards the septum. That is, the distal end of the sheath pushes against the proximal side of the proximal anchor 406 as an inner surface of the sheath slides over an outer surface of the lead body 400A.

FIG. 5 illustrates the relative positions of the anchors 404 and 406 when the anchor 406 is positioned against the septum (septum not shown). Here, the tines of the distal anchor 404 and the perpendicular portions 412 of the tines of the proximal anchor 406 are positioned a distance "d" from one another. As discussed above, the distance "d" may be substantially equal to or less than the corresponding width of the septum.

The use of a slideable proximal anchor 406 also may facilitate the use of a more secure mechanism for clamping the septum between the distal and proximal anchors. For example, the proximal anchor 406 may be slid to a desired position and a mechanism engaged to lock the proximal anchor 406 to that position on the lead 400. In various embodiments such a locking mechanism may be incorporated into the proximal anchor 406 and/or another component of the lead 400 (e.g., the lead body 400A or sensor housing).

FIGS. 4 and 5 illustrate an embodiment where the lead 400 incorporates a locking mechanism 416 for restricting movement of the proximal anchor 406. Through the use of such a mechanism the proximal anchor 406 may be pushed into a position whereby the proximal anchor 406 firmly pushes against the proximal side of the septum. As a result, the septum may be securely clamped between the two anchors 404 and 406 thereby securely fixing the lead 400 to the septum.

Figure 6:
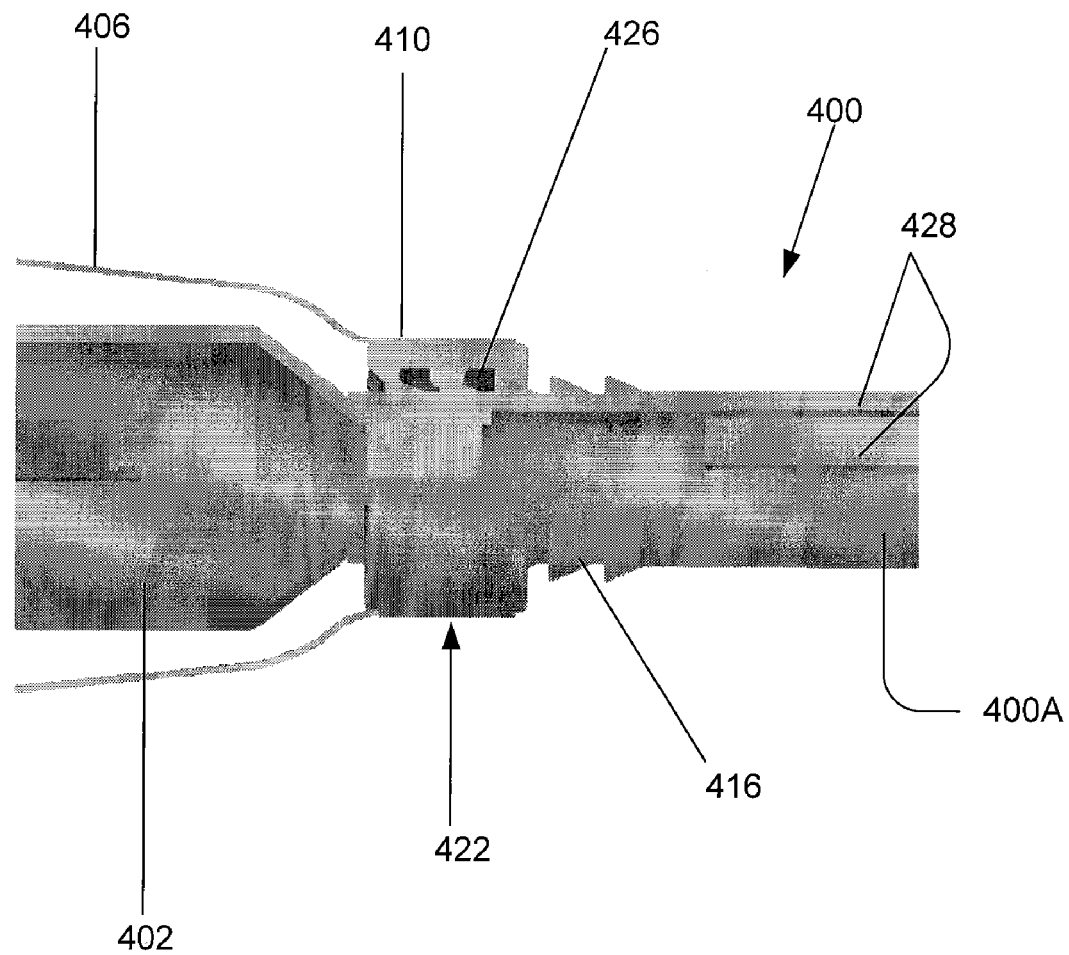
FIG. 6 is a simplified diagram illustrating one embodiment of a locking mechanism for a slideable anchor.

FIG. 6 illustrates one embodiment of a locking mechanism 422 in more detail. The lead body 400A includes one or more protrusions 416 (hereafter referred to as "ribs") that interact with one or more grooves 426 in the member 410 of the proximal anchor 406. The inside diameter of the member 410 may be slightly less than the outside diameter of the ribbed portion of the lead body 400A. In addition, the ribs 416 may be formed of a compressible material such as silicone rubber or other suitable material. As a result, the ends of the ribs 416 may bend to enable the ends to partially enter the grooves 426 thereby impeding movement of the proximal anchor 406 in the proximal direction once a rib 416 engages a groove 426.

The ribs 416 may be directional in that they may impart less (e.g., substantially less) resistance to movement of the proximal anchor 406 in the distal direction as opposed to the proximal direction. For example, as shown in FIG. 6, each rib 416 may have an inclined side and a vertical side.

In addition, one or both of the anchors 404 and 406 may be relatively flexible. Consequently, the anchors may provide some "give" to enable the proximal anchor 406 to be pushed to the next position (to the left in FIG. 6) of the locking mechanism.

It should be appreciated that various mechanisms and variations of such mechanisms may be employed to lock the proximal anchor 406 relative to the lead 400. For example, in some embodiments the ribs 416 may be located on the proximal anchor 406 while the grooves 426 are provided on the lead 400. In addition, the ribs and grooves may be shaped in a manner that differs from the shapes depicted in FIG. 6.

FIG. 6 also illustrates that the lead body 400A may incorporate one or more longitudinal grooves 428 that facilitate and/or restrict movement of the proximal anchor 406 relative to the lead body 400A. For example, the member 410 may include one or more protrusions on an inner surface (not shown) that ride within a groove 428. In this case, the interaction of the protrusion and the groove 428 may prevent the proximal anchor 406 from rotating around the lead body 400A.

Figure 7:
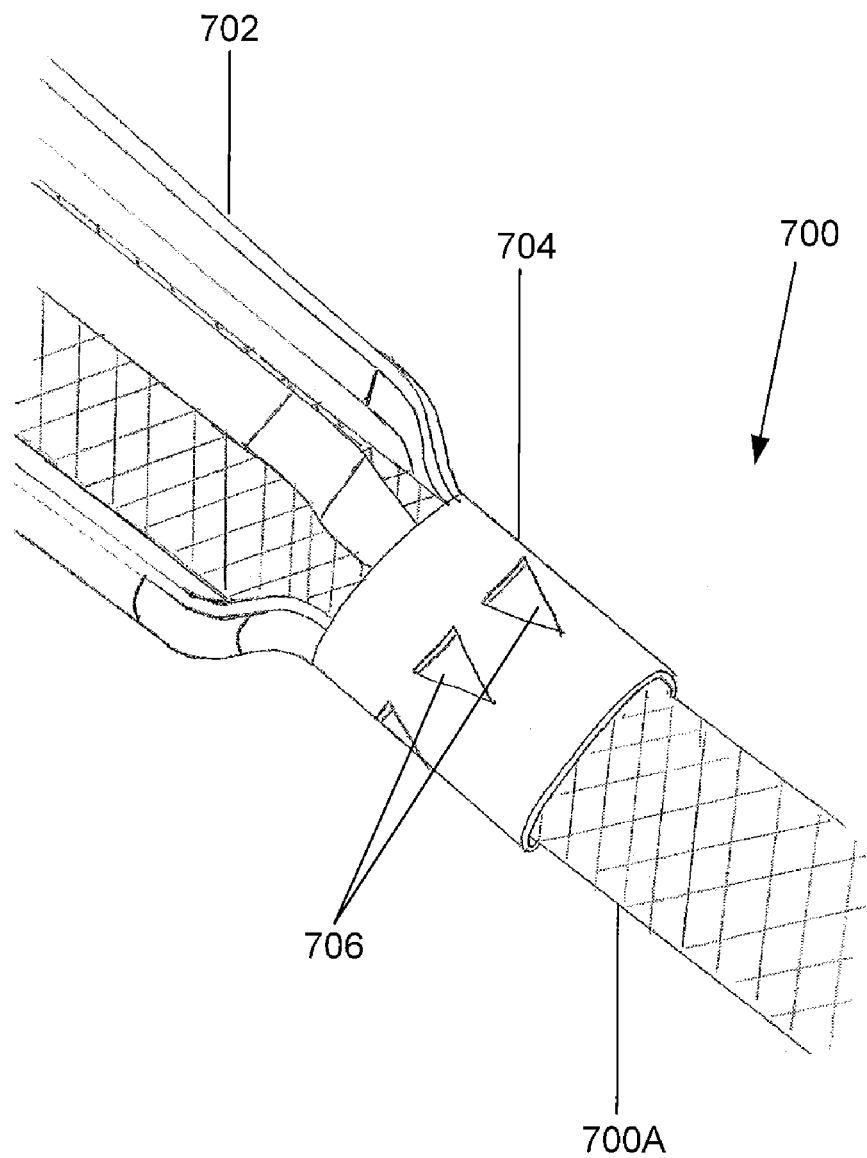
FIG. 7 is a simplified diagram illustrating one embodiment of a locking mechanism for a slideable anchor.

FIG. 7 illustrates another embodiment of a locking mechanism for a lead 700. Here, a ring-like member 704 for a proximal anchor 702 is adapted to slide along an outer surface of a lead body 700A. In addition, the member 704 includes one or more barbs 706 that engage or otherwise interact with the outer surface of the lead body 700A. Such an interaction may be better understood by reference to FIG. 8 that shows, in an exaggerated manner, that the barbs 706 protrude inward from the member 704 toward the outer surface of the lead body 700A. In this case, since the locking mechanism is located on the proximal anchor 702, the lead body 700A may have a relatively smooth exterior surface.

Figure 8:
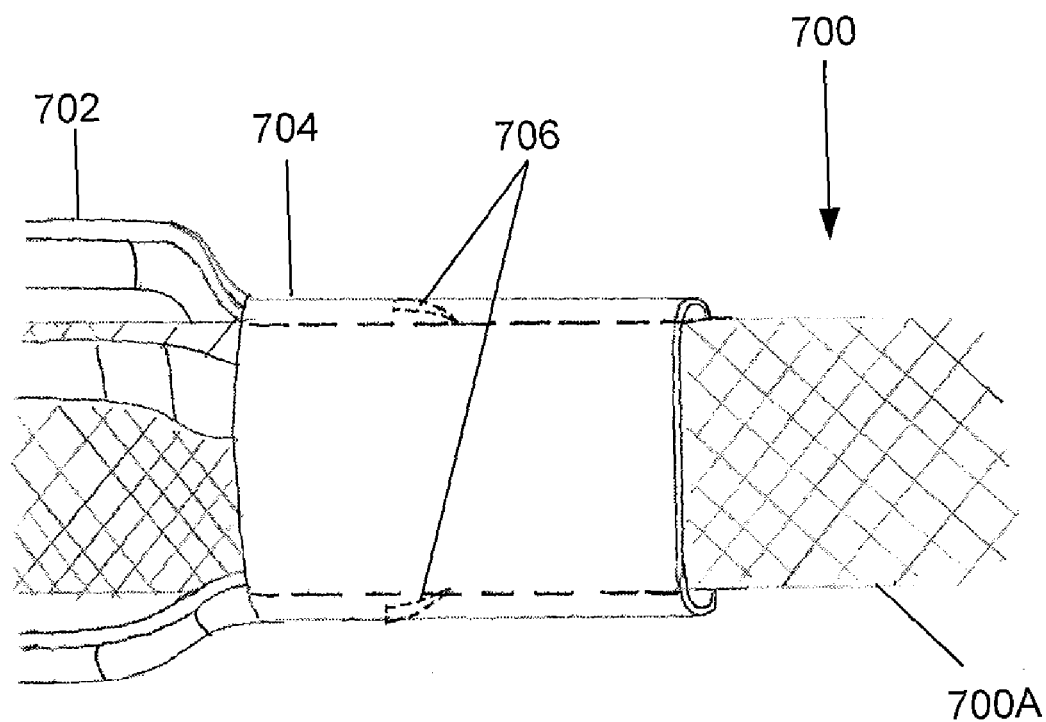
FIG. 8 is a simplified diagram illustrating another view of the locking mechanism of FIG. 7.

As illustrated by FIGS. 7 and 8, a barb 706 may be directional in nature. For example, a barb 706 may impart substantially more impedance (e.g., resistance) on movement of the proximal anchor 702 in the proximal direction than in the distal direction.

Again, it should be appreciated that various mechanisms and variations of such mechanisms may be employed to lock the proximal anchor 702 relative to the lead 700. For example, in some embodiments the barbs 706 may be located on the lead 700 (e.g., the lead body 700A). In addition, a barb 706 may take a form that differs from the form depicted in FIGS. 7 and 8.

Figure 9:
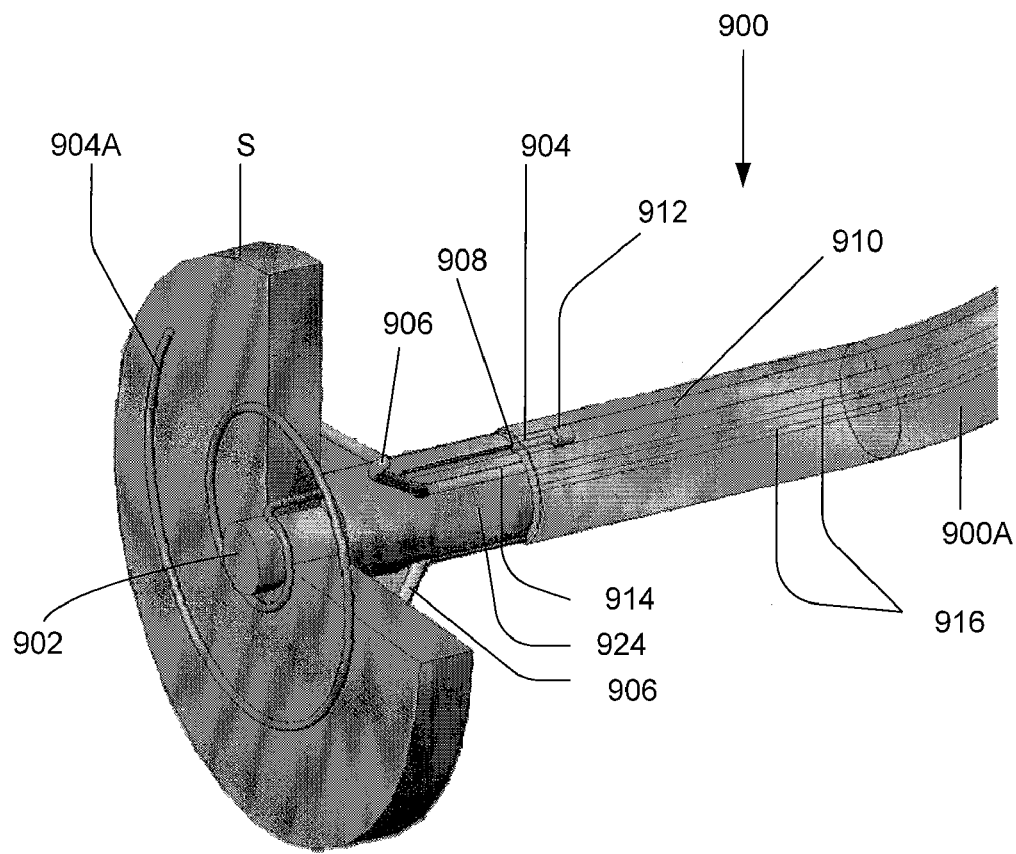
FIG. 9 is a simplified diagram of one embodiment of a lead including distal and proximal anchors.

FIG. 9 illustrates another embodiment of a lead 900 including a sensor 902 and anchors for fixing the lead to a septum S. Here, an elongated flexible member (hereafter referred to as a wire anchor 904) is adapted to slide within a lumen 910 in the lead 900. The wire anchor 904 is drawn into the lead 900 when the lead 900 is being routed to the implant site (see FIG. 10). Once the implant site has been reached, a distal end 904A of the wire anchor 904 is displaced from the lumen 910 via a port 922 in a housing 924 on a distal portion of the lead 900. Once freed from the confines of the lumen 910, the distal end 904A of the wire anchor 904 reorients to a predisposed orientation. In the example of FIG. 9, the predisposed orientation is in the form of a spiral lying substantially in a plane perpendicular to the axis of the lead 900.

The wire anchor 904 may thus be formed so that in its predisposed orientation it lies relatively flat against the distal wall of the septum S. In this way, the lead 900 may be firmly attached to the septum S yet have a relatively low profile in, for example, the left side of the heart.

The wire anchor 904 may be constructed of various materials to achieve the desired orientation properties. For example, the wire anchor 904 may comprise a biocompatible shape memory material or other suitable material. In some embodiments the wire anchor 904 is made from a memory metal such as Nitinol.

A wire anchor such as wire anchor 904 may be used to anchor the lead 900 to the septum S either independently or in combination with other types of anchors. As an example of the latter scenario, a distal wire anchor 904 may be employed along with a proximal anchor including tines 906. The tines 906 extend from the housing 924 to engage the proximal side of the septum S. In some embodiments the tines 906 may be under tension (or exert some other force) to clamp the septum S between the wire anchor 904 and the tines 906.

Alternatively, the lead 900 may be configured to provide a wire anchor such as wire anchor 904 on the proximal side of the septum S (not shown in FIG. 9). For example, the lead 900 may include a lumen for a proximal wire anchor and the lumen may terminate at a port in the housing 924 on the proximal side of the septum S. Thus, the vertical edge upon which port 922 resides may be located further to the right such that a proximal wire anchor exiting a port on the vertical edge may be adapted to reorient to an orientation that lies against the proximal side of the septum S. Thus, in practice, the lead 900 may be configured to provide a wire anchor such as wire anchor 904 on either side or both sides of the septum S.

FIG. 9 also illustrates that the lead 900 may include one or more conductors (e.g., wires) that couple the sensor 902 with an implantable cardiac device. In a typical embodiment, the conductors are routed through one or more lumens in the lead body 900A.

Figure 10:
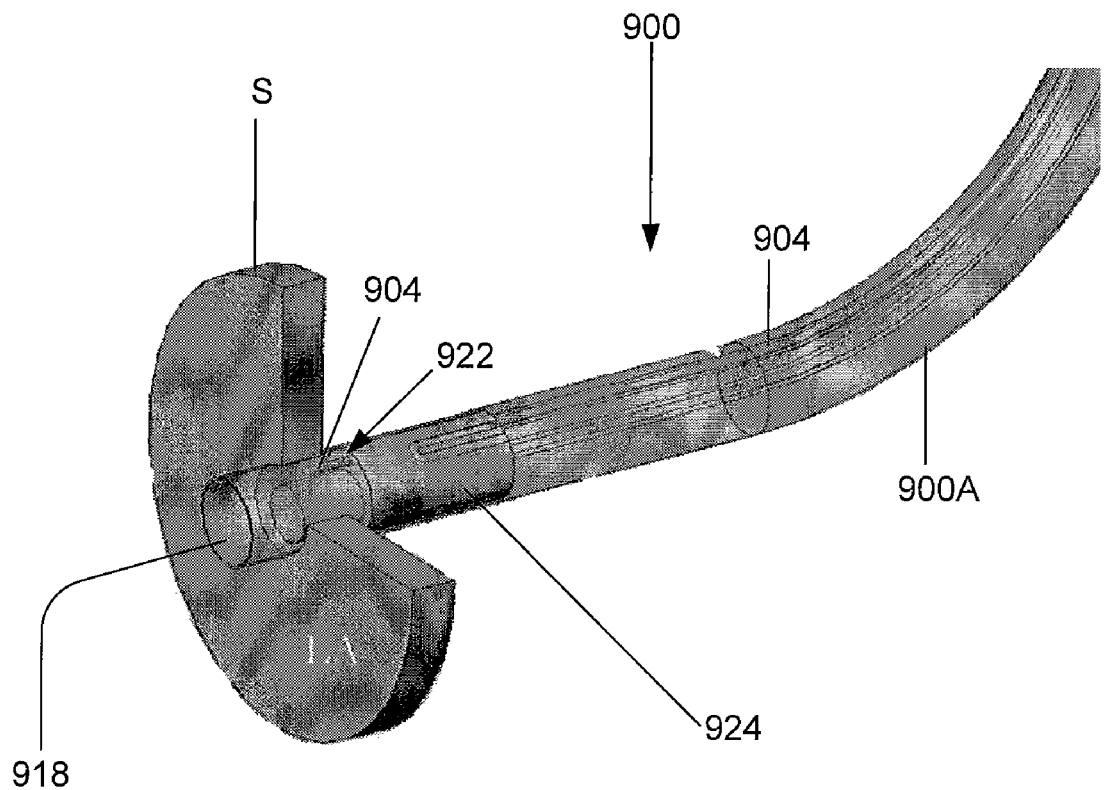
FIG. 10 is a simplified diagram of the lead of FIG. 9 with the distal anchor in a retracted position.

During initial deployment of the lead 900 to the implant site, the anchors may be drawn into the lead 900. In this way, the lead 900 may be passed through a sheath 918 that has been implanted to gain access to a distal side of a septum (e.g., the left atrium "LA") as shown in FIG. 10. For example, the wire anchor 904 may be drawing into the lead body 900A such that only a portion of the wire anchor 904 extends from the port 922. In addition, each tine 906 may be folded, drawn or otherwise manipulated into a channel or lumen 914 in the housing 924.

Figure 11:
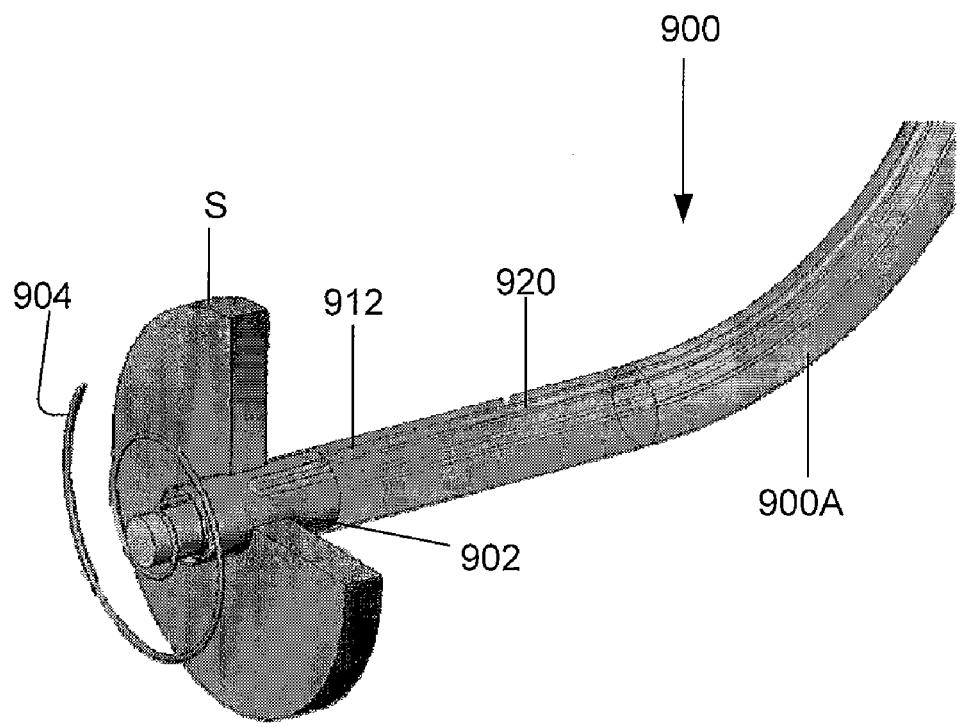
FIG. 11 is a simplified diagram of the lead of FIG. 9 with the distal anchor in a deployed position.

Referring to FIG. 11, the wire anchor 904 may include a connector 912 on its proximal end to facilitate connection to a stylet 920 or other similar instrument than may be used to reposition the wire anchor 904. In some embodiments the connector 912 is threaded to enable a complimentary threaded stylet 920 to connect to the wire anchor 904. The stylet 920 may thus be manipulated at a proximal end of the lead 900 (not shown) to push a portion of the wire anchor 904 out of the lumen 910 or draw the wire anchor 904 back into the lumen 910.

The connector 912 also may be sized to prevent the entire wire anchor 904 from passing through the port 922. For example, referring again to FIG. 9 the connector 912 may have a larger circumference than a lumen (not shown) in the housing 924 through which the wire anchor 904 passes to the port 922. In this case, the connector 912 will travel no further in the distal direction than the location identified by reference line 908.

Figure 12:
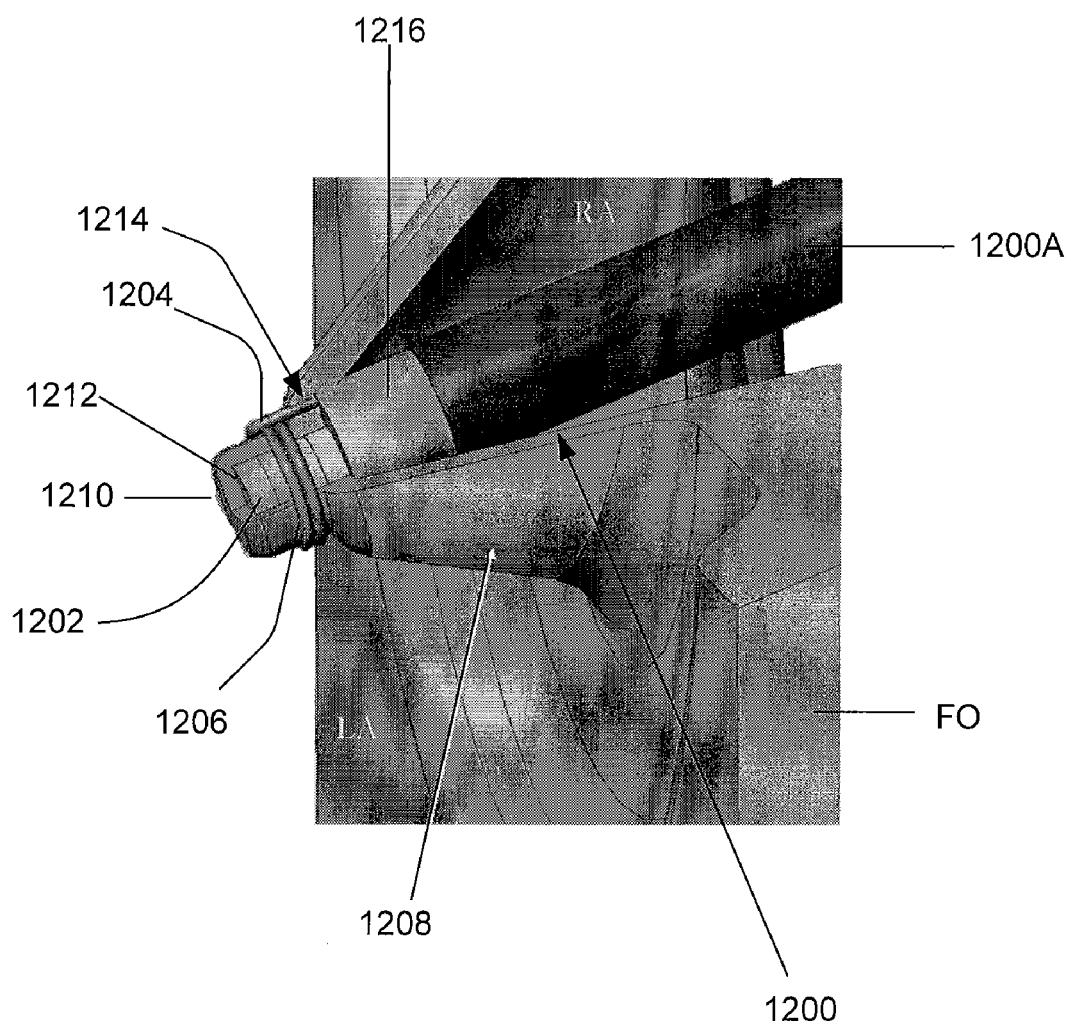
FIG. 12 is a simplified diagram of one embodiment of a lead including a distal anchor that secures a portion of a heart wall around a distal portion of a lead.

FIG. 12 illustrates an embodiment of a lead 1200 including a sensor 1202 and a wire anchor 1204 adapted to wrap around a distal portion of the lead 1200 to hold a portion of the septum against the lead 1200. In the example of FIG. 12, the lead 1200 has been routed through the right atrium ("RA") and forced against the fossa ovalis ("FO"). As a result, a portion 1208 of the fossa ovalis has been distorted (e.g., stretched) such that the portion 1208 extends around a distal portion of the lead 1200.

The lead 1200 and the wire anchor 1204 may be constructed in a similar manner as lead 900 and wire anchor 904 discussed above. In the embodiment of FIG. 12, however, the wire anchor 1204 is adapted to have a predisposed orientation that wraps around a distal portion (e.g., sensor 1202) of the lead 1200. Thus, when the lead 1200 is in route to the implant site, the wire anchor 1204 may be withdrawn into a lumen in a lead body 1200A.

Once the lead 1200 is positioned as shown in FIG. 12, the wire anchor 1204 may be forced in a distal direction out of a port in a distal housing 1216 through a hole 1214 in the fossa ovalis. In some embodiments the wire anchor 1204 may be used to puncture through the fossa ovalis to create the hole 1214. Alternatively, the hole 1214 may be made using a piercing tool (not shown) prior to delivery of the lead 1200 to the implant site.

The wire anchor 1204 may be adapted such that the inner circumference of a loop 1206 formed around the sensor 1202 is slightly larger than the outer circumference of the sensor 1202. In this way, the loop 1206 may securely clamp a distorted portion of the fossa ovalis to the end of the sensor 1202 while reducing the likelihood of the wire anchor 1204 cutting through or migrating through the fossa ovalis tissue. As a result, a diaphragm 1212 located at a distal end of the sensor 1202 may be positioned to obtain pressure readings from the left atrium ("LA") through a portion 1210 of the fossa ovalis.

As may be observed from FIG. 12, the sensor 1202 may detect pressure from the left atrium without being exposed to the left atrium. Advantageously, the distal end of the wire anchor 1204 is the only foreign component in the left atrium. Moreover, there may be little or no tissue overgrowth in the vicinity of the sensor diaphragm 1212 because the sensor diaphragm 1212 is covered by native tissue. Consequently, the sensor 1202 may not be subjected to drift that may otherwise result from such tissue overgrowth. This, in turn, may reduce or eliminate the need for calibration to compensate for such drift.

Figure 13:
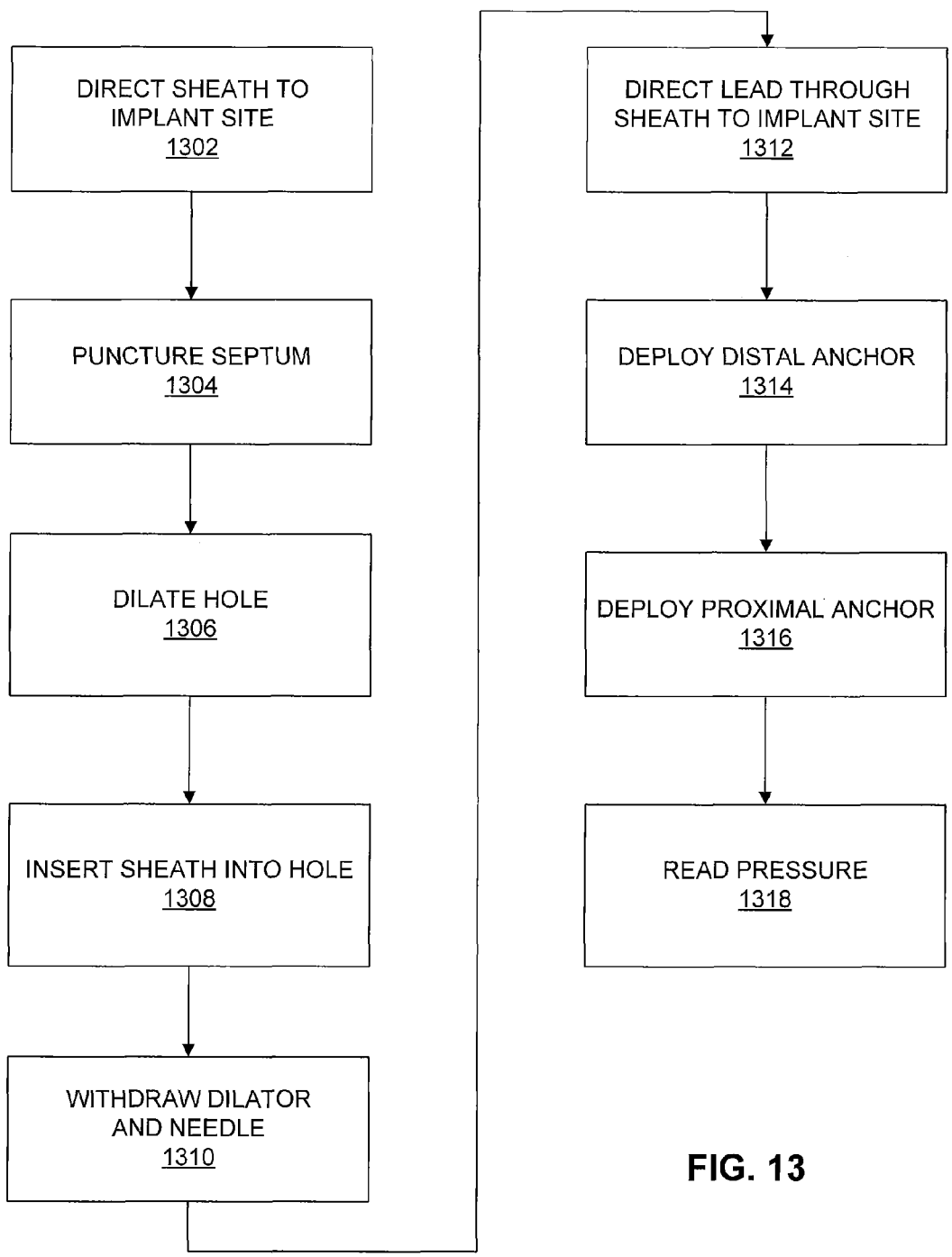
FIG. 13 is a flow chart of one embodiment of operations that may be performed to implant a transseptal lead.

Referring now to FIGS. 13 and 14 one embodiment of a lead delivery procedure will be discussed in some detail. As represented by block 1302 in FIG. 13, a distal end of an instrument 1400 (FIG. 14A) may be initially introduced into the heart via the right atrium ("RA") using known techniques. For example, the instrument 1400 may accept a stylet that enables the instrument 1400 to be manipulated in a desired direction through the venous system and the heart. Once the distal end 1402 of the instrument 1400 reaches the septum, the procedure may involve probing via the distal end 1402 to identify an acceptable implant site (e.g., the fossa ovalis) on the septum.

Figure 14A:
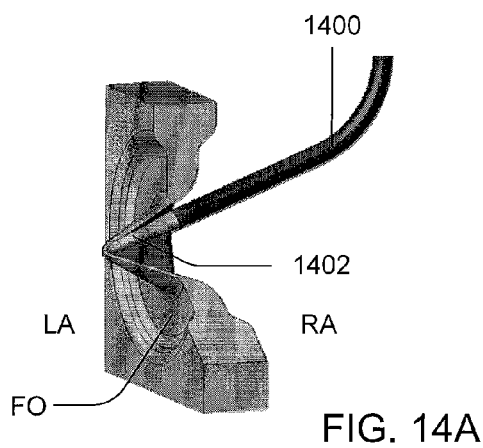
FIGS. 14A-14F, illustrates one embodiment of instruments used to implant a transseptal lead.
Figure 14B:
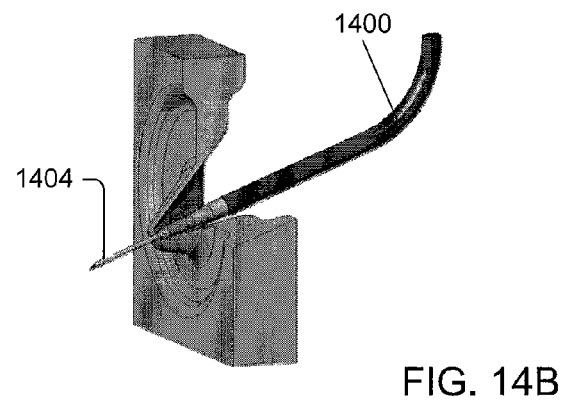

As represented at block 1304, a transseptal needle 1404 or other suitable puncturing instrument may be routed through the instrument 1400 to create a hole in the septum (FIG. 14B). At block 1306, a dilator portion 1402 of the instrument may then be used to increase the size of the hole 1406 (FIG. 14C).

Figure 14D:
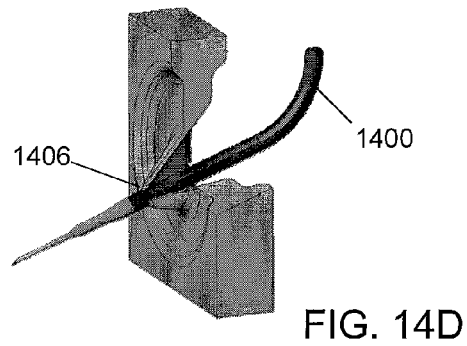
Figure 14C:
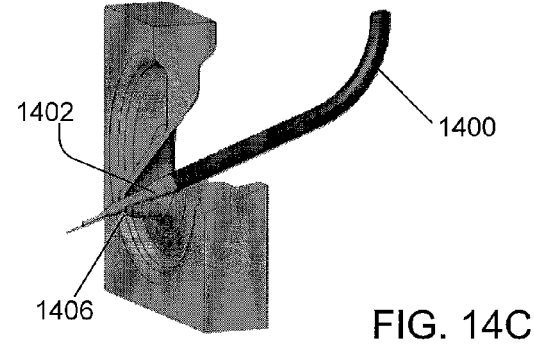
Figure 14E:
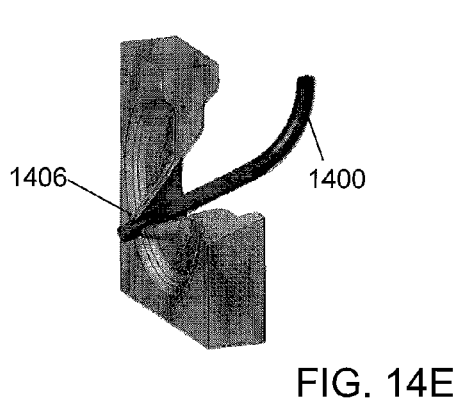

Next, at block 1308, a sheath portion of the instrument 1400 is passed through the hole 1406 (FIG. 14D). As represented by block 1310, the dilator 1402 and needle 1404 may then be removed, leaving the hollow sheath at the implant site (FIG. 14E).

Figure 14F:
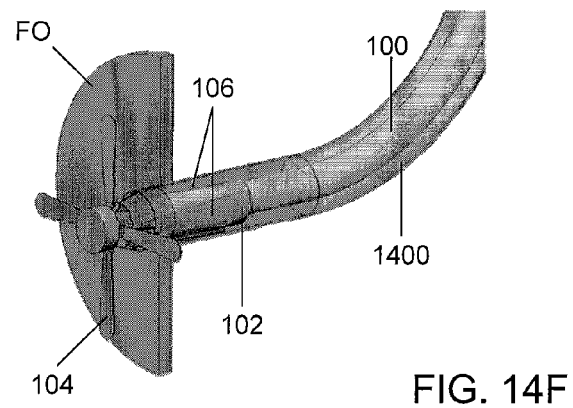

As represented by block 1312, the lead 100 is inserted into the sheath 1400 and directed to the implant site. At block 1314, the distal portion of the lead 100 is maneuvered through the septum so that a distal anchor 104 is deployed into the left atrium (FIG. 14F). As discussed above, the distal anchor 104 may thus be adapted to be disposed between an orientation lying substantially parallel to the lead 100 (for delivery through the sheath) and an orientation extending from the lead 100 (e.g., as shown in FIG. 14F).

At block 1316, the sheath 1400 is withdrawn to deploy a proximal anchor 106. Also as discussed above, the proximal anchor 106 may be adapted to be disposed between an orientation lying substantially parallel to the lead 100 (e.g., bent in a proximal direction for delivery through the sheath) and an orientation extending from the lead 100 (e.g., as shown in FIG. 14F). In some embodiments this may involve moving and locking the proximal anchor 106 to a position adjacent the septum.

The lead 100 may thus be secured to the septum such that at least a portion of a pressure sensor 102 at a distal end of the lead 100 protrudes into the left atrium. In this way, the sensor 102 may be used to accurately obtain pressure readings from the left atrium (block 1318).

As discussed above, in some embodiments the anchors 104 and 106 are positioned a pre-defined distance apart on the lead 100. For example, the lead may be constructed so that the spacing between the anchors 104 and 106 is approximately equal to the thickness of the septum in the area of the hole 1406.

Alternatively, in some embodiments one or more of the anchors are attached to the lead 100 in a manner that enables the position of the anchor to be adjusted. For example, the anchor 106 may be slideably mounted to the lead 100 so that the anchor 106 may be moved toward the anchor 104 to firmly secure (e.g. via a locking mechanism) the anchors 104 and 106 to the septum.

Various control apparatus (not shown) may be attached to the proximal end of the instrument 1400 and/or the lead 100. For example, mechanisms may be provided for moving stylets or guide wires, or other components (not shown) in the lead 100. The control apparatus may then be removed from the lead 100 when the implantable cardiac device (not shown) attached to proximal end of the lead 100 is implanted in the patient.

It should be appreciated from the above that the various structures and functions described herein may be incorporated into a variety of apparatuses (e.g., a lead) and implemented in a variety of ways. For example, fixation structures and locking mechanisms may be implemented and incorporated into a lead in accordance with the teachings herein in a variety of ways other than the ways specifically mentioned herein. Such structures may be made of a variety of materials consistent with the teachings herein. Moreover, the leads described above may be implanted against or across any cardiac wall including, for example, the atrial septum or the ventricular septum. In addition, various types of sensors may be incorporated into a lead.

While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A lead adapted to obtain pressure readings from a distal side of a wall of a heart, comprising:
   a lead body;
   an elongated flexible member adapted to slide within the lead body such that a portion of the member is displaceable from a distal portion of the lead body, wherein the displaceable portion of the member is adapted to reorient to a curved orientation to engage a side of a wall of a heart; and
   a pressure sensor attached to the lead body and adapted to obtain pressure readings from the distal side of the heart wall;
   wherein the displaceable portion of the member is adapted to form a loop around a distal portion of the lead to clamp a portion of the heart wall between the loop and the distal portion of the lead body.

2. The lead of claim 1 wherein the pressure sensor is located on a distal end of the lead body and the displaceable portion of the member is adapted to form a loop around the pressure sensor to clamp a portion of the heart wall between the loop and the pressure sensor.

3. The lead of claim 2 wherein a distal end of the pressure sensor comprises a diaphragm.

4. The lead of claim 1 wherein the lead is adapted to be routed through a right atrium and forced against a fossa ovalis such that a portion of the fossa ovalis extends around the distal portion of the lead, and wherein the loop is adapted to clamp the portion of the fossa ovalis around the distal portion of the lead.

* * * * *